United States Patent [19]

Bakshi et al.

[11] Patent Number: 4,560,800

[45] Date of Patent: Dec. 24, 1985

[54] ISOLATION OF M,M'-DINITROBENZOPHENONE

[75] Inventors: Kiran R. Bakshi, Murrysville; Adrian D'Souza, Pittsburgh; Edward T. Sabourin, Allison Park, all of Pa.

[73] Assignee: Gulf Research & Development Co., Pittsburgh, Pa.

[21] Appl. No.: 650,881

[22] Filed: Sep. 17, 1984

[51] Int. Cl.$^4$ .............................................. C07C 45/61
[52] U.S. Cl. .................................. 568/306; 528/222; 528/229; 564/328
[58] Field of Search .......................................... 568/306

[56] References Cited

U.S. PATENT DOCUMENTS

| | | | |
|---|---|---|---|
| 4,352,942 | 10/1982 | Onopchenko et al. | 568/306 |
| 4,361,704 | 11/1982 | Onopchenko et al. | 568/306 |
| 4,413,144 | 11/1983 | Tappe et al. | 568/306 |

Primary Examiner—James H. Reamer
Assistant Examiner—Vera C. Clarke
Attorney, Agent, or Firm—D. E. Keith; D. Stenl; R. C. Gaffney

[57] ABSTRACT

A process for the preparation and recovery of m,m'-dinitrobenzophenone and which comprises reacting benzophenone with nitric acid in oleum; adjusting the reaction product to a water content from 12 to 30 weight percent; and extracting the m,m'-dinitrobenzophenone with a chlorinated hydrocarbon solvent.

21 Claims, No Drawings

ISOLATION OF M,M'-DINITROBENZOPHENONE

BACKGROUND OF THE INVENTION

1. Field of the Invention

The present invention relates to the process for preparing m,m'-dinitrobenzophenone by reacting benzophenone with nitric acid in oleum and isolating the m,m'-dinitrobenzophenone from the reaction product.

2. Description of the Prior Art

When benzophenone is reacted with nitric acid, a product can be obtained containing an isomeric mixture of dinitrobenzophenones, including o,o'-, o,m'-, m,m'-, m,p'- and p,p'-dinitrobenzophenones, which, in turn, can be subjected to hydrogenation to obtain an isomeric mixture of the corresponding diaminobenzophenones. The latter mixture can be reacted with 3,4,3',4'-benzophenone tetracarboxylic dianhydride (BTDA) to obtain a polyimide resin. Although the m,m'-, m,p'- and p,p'-diamino benzophenones in said latter mixture will react satisfactorily with BTDA to form desired long-chain polyimide resins, the ortho-diaminobenzophenones will react with BTDA to a far lesser extent, resulting in a mixture of long and relatively short polyimide resins. This is believed to be the result of hydrogen bonding between an ortho amine hydrogen and the carbonyl, which reduces the basicity of the compound and renders the compound less reactive with BTDA. It would be highly desirable, therefore, to reduce the content of ortho-substituted isomers of dinitrobenzophenones and substantially increase the content of m,m'-dinitrobenzophenone in a mixture containing the same.

In accordance with the teachings of U.S. Pat. No. 4,361,704 to Onopchenko, et al., benzophenone can be reacted with nitric acid to obtain a product containing an isomeric mixture of dinitrobenzophenones predominating in m,m'-dinitrobenzophenone, while substantially reducing the content of the isomers containing an ortho-nitro substituent with virtual disappearance of the o,o'-dinitrobenzophenone. In the Onopchenko, et al. process, benzophenone is reacted with nitric acid in oleum while maintaining critical weight ratios of benzophenone, sulfuric acid and sulfur trioxide in the feed.

Onopchenko, et al. teach in Column 2, lines 34 et. seq. that the dinitribenzophenones can be recovered from the reaction mixture by pouring the reaction mixture over ice and the resulting slurry can be subjected to filtration. The resulting filter cake however is a colored (i.e., tan) solid which requires a considerable amount of time and effort in continuous crushing, washing and refiltering to remove the impurities which are causing the coloration problem.

SUMMARY OF THE INVENTION

We have discovered an improved procedure for the recovery of the dinitrobenzophenones from the product of reacting benzophenone with nitric acid in oleum which, surprisingly, recovers in excess of 90 percent of the dinitrobenzophenones in a single solvent extraction stage. This improved procedure comprises contacting the product from the reaction of benzophenone with nitric acid and oleum with a solvent extracting amount of a chlorinated hydrocarbon having from one to six carbon atoms under solvent extraction conditions and wherein the free water content in the solvent extraction zone is from 12 to 30 weight percent based on the total weight of the solvent-free material in the solvent extraction zone. The chlorinated hydrocarbon containing the m,m'-dinitrobenzophenone is thereafter separated and the m,m'-dinitrobenzophenone recovered. The separated chlorinated hydrocarbon containing the dinitrobenzophenones is a clear liquid containing no colored impurities and the dinitrobenzophenones can be recovered from the chlorinated solvent by normal techniques.

The process of this invention can be practiced to recover dinitrobenzophenones from the reaction product of benzophenone with nitric acid in oleum. Preferably, the process of this invention is utilized to recover dinitrobenzophenones from the product of the process described in U.S. Pat. No. 4,361,704. In accordance with the '704 Patent, the critical weight ratio of benzophenone, sulfuric acid (as 100 percent sulfuric acid) and sulfur trioxide must be in the range of about 1:3:1 to about 1:25:5, but preferably in the range of about 1:2:2 to about 1:15:4. The sulfuric acid and sulfur trioxide employed can be satisfied by the use of oleum. By "oleum" we mean to include concentrated sulfuric acid containing sulfur trioxide. The amount of sulfur trioxide, on a weight basis relative to the total weight of sulfuric acid and sulfur trioxide, will be in the range to satisfy the critical weight ratios defined above, for example, in the range of about 5 to about 65 percent, preferably about 10 to about 35 percent. Oleum suitable for use herein can be prepared, for example, by adding gaseous or liquid $SO_3$ to concentrated sulfuric acid. It is believed that sulfur trioxide when dissolved in, or added to, sulfuric acid readily forms $H_2S_2O_7$ and higher polysulfuric acids [R. Gillespie, J. Chem. Soc., 2493 (1950)].

The benzophenone, nitric acid, sulfuric acid and sulfur trioxide are brought together, with the weight ratios of benzophenone, sulfuric acid and sulfur trioxide being within the critical ranges defined above. The amount of nitric acid is not critical and should be sufficient, stoichiometrically, to place one nitro group on each of the rings of the benzophenone being treated. To assure substantially complete reaction, amounts in excess of those required stoichiometrically to obtain dinitrobenzophenones can be used, for example, up to about 10 weight percent, or even higher. The concentration of the nitric acid used can vary over a wide range, for example from about 50 to about 100 weight percent aqueous nitric acid, preferably from about 67 to about 95 weight percent aqueous nitric acid can be employed based on the weight of the reaction mixture.

The reaction can be carried out for example by stirring the reaction mixture while heating the same in a temperature range of about 5° to about 120° C., preferably about 10° to about 90° C., for about 10 minutes to about 120 hours, or even longer, preferably for about one-half to about 24 hours. In a preferred embodiment in order to further control the reaction to assure obtaining the desired isomeric distribution, the process is carried out in a plurality of stages. In a first stage, for example, the temperature is maintained in a range of about 5° to about 50° C., preferably about 10° to about 30° C., for about 10 minutes to about 10 hours, preferably for about one-half to about 8 hours. In a second stage the reaction mixture is maintained in the temperature range of about 20° to about 120° C., preferably about 50° to about 90° C., for about one-half to about 5 hours, preferably about 1 to about 3 hours. The pressure is not critical and elevated pressures up to about 100 pounds per square inch gauge (about 0.7 Mpa), or even higher, can be used, although atmospheric, or ambient, pressure is preferred.

It has been found in accordance with the invention that by properly adjusting the water content of the above nitration reaction mixture, that it is possible to extract the dinitrobenzophenones into a chlorinated hydrocarbon solvent and leave the bulk of the impurities in the aqueous phase. The final traces of impurities can readily be removed by an aqueous caustic extraction of the organic phase. Solvent stripping and/or precipitation with an organic non-solvent produces dinitrobenzophenones essentially free from impurities.

The water content of the nitration reaction mixture or product can initially be adjusted by the addition of water so that the free water content of the reaction product is within the range from about 12 to about 30 weight percent. This water adjustment can occur before or after the addition of the chlorinated hydrocarbon solvent. Preferably the adjustment occurs after the addition of the solvent since the solvent can serve the added function of a heat sink. This 12 to 30 weight percent free water is the total water in the reaction product (excluding the chlorinated solvent) including water present in the nitric acid; water formed during the reaction; and the water added after the reaction is complete less any water reacted with the $SO_3$ in the oleum to form $H_2SO_4$. It is always necessary to add water since the presence of 12 to 30 weight percent free water during the nitration reaction would reduce the initial selectivity because the ortho isomer would not be eliminated. The initial reaction product contains no free water as any free water present in the nitric acid or formed during the reaction reacts with the $SO_3$ in the oleum as fast as it forms to give more $H_2SO_4$. Water must be added slowly with vigorous agitation. The dichloroethane can help remove heat by refluxing if an appropriate condenser is attached. The presence of less than 12 weight percent free water in the total reaction product is undesirable because incomplete extraction of the product occurs. The presence of more than 30 weight percent water in the reaction product is undesirable because the interface becomes indistinct and emulsions form. Preferably the weight percent water in the reaction product is from 12 to 30 weight percent and more preferably the adjusted concentration of water is from 15 to 25 weight percent of the solvent-free materials present in the extraction zone.

The nitration reaction product having a water content from 12 to 30 weight percent is suitably contacted with a solvent extracting amount of a chlorinated hydrocarbon having from one to six carbon atoms under solvent extraction conditions. Preferably the chlorinated hydrocarbon has from two to four chlorine atoms and is more preferably an aliphatic hydrocarbon having from two to four chlorine atoms. While 1,2-dichloroethane is the preferred chlorinated hydrocarbon, the following solvents can also be employed:
dichloromethane
1,1,1-trichloroethane
1,1,2-trichloroethane
1,1,2,2-tetrachloroethane
1,2-dichlorobenzene
carbon tetrachloride
chloroform The amount of the chlorinated hydrocarbon solvent to employ is not critical and suitable amounts include a volume ratio of solvent to nitration reaction mixture from 0.5:1 to 10:1 or more, usually about 0.9:1 to 3:1.

Similarly the solvent extraction conditions are not critical with temperatures normally in the range of 50° to 60° C. and a pressure of atmospheric although higher or lower pressures can be employed. It is however important to keep the temperature above about 40° C. to maintain solubility of the dinitrobenzophenones in the chlorinated hydrocarbon solvent. The upper temperature for the solvent extraction is limited by the volatility of the product which, of course, is affected by pressure. Appropriate variations of temperature and pressure without departing from the spirit and scope of this invention would be obvious to those having ordinary skill in this art.

The solvent extraction of the aqueous nitric acid product mixture can, of course, occur in multiple stages but it has been found quite surprisingly that more than 90 percent of the dinitrobenzophenones in the nitric acid reaction product can be recovered in a single extraction phase using the process of this invention. The chlorinated hydrocarbon solvent phase can, of course, be readily separated from the aqueous nitric acid mixture, and in most instances is substantially water white. The last traces of impurities can readily be removed by an aqueous caustic extraction of the organic phase if desired. The dinitrobenzophenones can then be recovered from the chlorinated hydrocarbon solvent phase by precipitation from an organic non-solvent preferably with initial removal of at least a portion of the solvent (i.e., usually 40 to 70 volume percent of the solvent). The resulting dinitrobenzophenones are essentially free from impurities. Suitable organic non-solvents to employ are aliphatic hydrocarbons having from 5 to 10 carbon atoms.

DESCRIPTION OF PREFERRED EMBODIMENTS

The process defined and claimed herein can be illustrated by the following.

EXAMPLE 1

A simulated reaction mixture was prepared by dissolving 20 grams of m,m'-dinitrobenzophenone in 50 milliliters of concentrated sulfuric acid and 50 milliliters of 20 percent oleum. 100 milliliters of 1,2-dichloroethane was added to this reaction mixture. The mixture was stirred vigorously for 10 minutes at about 20° C. and then permitted to settle into aqueous and non-aqueous layers. The dichloroethane layer was separated and washed with an equal volume of 10 percent aqueous sodium hydroxide and then water. Stripping of the solvent produced only traces of dinitrobenzophenone.

EXAMPLE 2

Example 1 above was repeated except the stirring or contacting of 1,2-dichloroethane with the dinitrobenzophenone occurred at 50° C. Similar results were obtained.

A series of runs was made the same as Example 2 except varying amounts of water were added to the reaction mixture. These runs are summarized in Table I below along with the results of Examples 1 and 2.

TABLE I

| Example No. | Temp. °C. | Added Water, g | WT % $H_2O$ in Extraction Mixture | Recovered $DNBZP^a$; g; $\%^b$ |
|---|---|---|---|---|
| 1 | ambient | 0 | 0 | Trace |
| 2 | 50 | 0 | 0 | Trace |

TABLE I-continued

| Example No. | Temp. °C. | Added Water, g | WT % H₂O in Extraction Mixture | Recovered DNBZP[a]; g; %[b] |
|---|---|---|---|---|
| 3 | 50 | 16 | 7.2 | 4.0 g, 20 |
| 4 | 50 | 30 | 12.7 | 7.5 g, 37.5 |
| 5 | 50 | 50 | 19.6 | 18.7 g, 93.5 |
| 6[c] | 50 | 50 | 19.6 | 0.8 g, 4 |

[a]Dinitrobenzophenones
[b]Means % of DNBZP theoretically possible.
[c]Second Extraction of acid phase from Example 5.

Referring to Table I above, it can be seen that when the water content of the product is adjusted to about 20 weight percent that over 90 percent of the dinitrobenzophenone is recovered in a single extraction step (Example 5) while an additional 4 percent can be recovered in a second extraction (Example 6).

EXAMPLE 7

A nitrating mixture was prepared by adding 165 grams of 90 weight percent aqueous nitric acid over a period of 30 minutes to 570 grams of well-stirred oleum containing concentrated sulfuric acid and 22.5 weight percent sulfur trioxide while maintaining the temperature of the resulting mixture during the stirring procedure at about 10° to about 15° C. Two hundred grams of benzophenone were gradually dissolved over a period of 60 minutes in 1900 grams of oleum containing 22.5 weight percent sulfuric acid while maintaining the temperature of the resulting mixture at about 10° to about 20° C. With vigorous stirring and cooling the nitrating mixture of acids prepared above was gradually added to the benzophenone mixture over a period of 1.5 hours at about 10° to about 15° C. The resulting mixture was allowed to warm to 25° C. and was held at this temperature, with stirring, for a period of 30 minutes. The reaction mixture was heated to 70° C. and held for 2 hours. The treatment of this product to recover the dinitrobenzophenones is described in Example 14 below.

A series of runs was made which were substantially the same as Example 7 above, except the proportions of oleum and SO₃ were adjusted slightly from run to run to reflect the changes in free SO₃ concentration. Nitration conditions remained the same for each run except the final heat soak was at 90° C. instead of 70° C. The reaction mixture was then cooled and 1,500 milliliters of 1,2-dichloroethane were added. While the mixture was vigorously stirred, water was added carefully to maintain the temperature at about 50°-60° C. When the addition of water was complete, stirring was stopped and the aqueous and organic layers were separated while maintaining the temperature to prevent crystallization.

The upper dichloroethane layer was extracted with 500 milliliters of 10 percent aqueous sodium hydroxide and washed with 500 milliliters of water. The dichloroethane was then stripped until a volume of about 500 milliliters was attained. This solution was added to about 2,000 milliliters of hexane to precipitate the desired dinitrobenzophenone product as a readily filterable white powder. Table II below summarizes the results of these runs. In all of the runs in Table II, the HPLC (High Performance Liquid Chromatography) analysis showed the isomer composition to be 95±2 weight percent m,m'-dinitrobenzophenone and the remainder m,p'-dinitrobenzophenone.

TABLE II

| Example No. | HNO₃, g | Oleum, g | (% Free SO₃) | Benzophenone, g | Added Water, g | Final H₂O Concentration (WT % of the Mixture) | Isolated DNBZP, g |
|---|---|---|---|---|---|---|---|
| 8 | 165 | 2470 | (20) | 200 | 450 | (12.0) | 192 |
| 9 | 165 | 2470 | (20) | 200 | 550 | (14.6) | 223 |
| 10 | 165 | 1970 | (28) | 200 | 500 | (15.2) | 224 |
| 11 | 165 | 1970 | (26) | 200 | 500 | (15.5) | 220 |
| 12 | 165 | 1970 | (28) | 200 | 1000 | (27.1) | 231 |
| 13 | 165 | 1970 | (28) | 200 | 1200 | (32.0) | Partial Emulsion Further Addition of Water up to 2,500 ml (50.3%) Resulted in Total Emulsion |

Referring to Table II, it can be seen when the final concentration of water is about 32 percent, a partial emulsion is obtained and it was noted that the further addition of water (2,500 milliliters or 50.3 percent) resulted in a total emulsion.

It is to be noted in Example 8 that the final water concentration was 12 percent of the mixture. This 12 percent was calculated by dividing the total free water present (394.91 grams) by the total solvent-free material in the extraction zone (3285 grams) and multiplying by 100. The total free water is the sum of the water present in the HNO₃ (10 percent times 165 grams or 16.5 grams); the water made during the reaction (two moles of water per mole of benzophenone or 39.56 grams of water); the water added (450 grams) less the water consumed reacting with the SO₃ (20 percent free SO₃ in oleum or 6.175 moles times 18 or 111.15 grams of water). The total solvent-free material is the sum of 200 grams of benzophenone; 165 grams of HNO₃; 2470 grams of oleum and 450 grams of added water.

EXAMPLE 14

The reaction product from Example 7 above was cooled, poured over 2,000 grams of cracked ice-water mixture and filtered. The resulting solids were tan colored indicating the presence of impurities. These impurities, besides importing undesired color properties, serve as catalyst deactivators for any hydrogenation catalyst used to convert the nitro compound to the corresponding amine. The recovered solids were washed twice, each time with 1,000 milliliters portions of water, then with 1,000 milliliters of 10 weight percent aqueous sodium hydroxide, and finally, twice, each time, with 1,000 milliliters of water, until the washings were found to be neutral. Refiltering was of course required for each step and the reaction product was so fine that it tended to clog the filter, making the filtering process very difficult and time consuming. The solids were then dried in a vacuum oven at 100° C. for 16 hours, resulting in the recovery of 252 grams of dinitrobenzophenones. HPLC analysis showed the isomer composition to be 93.7 weight percent m,m'-dinitrobenzophenone and 6.3 weight percent m,p'-dinitrobenzophenone.

Obviously many modifications and variations of the invention, as hereinabove set forth, can be made without departing from the spirit and scope thereof and, therefore, only such limitations should be imposed as are indicated in the appended claims.

We claim:

1. A process for preparing m,m'-dinitrobenzophenone which comprises:

reacting benzophenone with nitric acid and oleum to form a first reaction product containing m,m'-dinitrobenzophenone;

passing said first reaction product to a solvent extraction zone;

contracting said first reaction product in said solvent extraction zone with a solvent extracting amount of a chlorinated hydrocarbon having from one to six carbon atoms under solvent extraction conditions and wherein the water content in said solvent extraction zone is from about 12 to about 30 weight percent based on the weight of solvent-free material in said extraction zone;

separating said chlorinated hydrocarbon from said first reaction product; and recovering m,m'-dinitrobenzophenone from said separated chlorinated hydrocarbon.

2. A process according to claim 1 wherein the weight ratios of benzophenone, sulfuric acid and sulfur trioxide in said oleum are in the range of about 1:2:2 to about 1:15:4.

3. A process in accordance with claim 2 wherein said chlorinated hydrocarbon has from two to four chlorine atoms.

4. A process in accordance with claim 3 wherein said chlorinated hydrocarbon is 1,2-dichloroethane.

5. A process in accordance with claim 2 wherein the volume ratio of said chlorinated hydrocarbon to said first reaction product is from 0.5:1 to 10:1.

6. A process in accordance with claim 1 wherein said m,m'-dinitrobenzophenone is recovered by precipitating the dinitrobenzophenone in a hydrocarbon non-solvent.

7. A process in accordance with claim 6 wherein at least a portion of said chlorinated hydrocarbon is removed prior to contact with said non-solvent.

8. A process in accordance with claim 7 wherein from about 40 to about 70 volume percent of the chlorinated hydrocarbon is removed prior to contact with said non-solvent.

9. A process in accordance with claim 6 wherein the non-solvent is a hydrocarbon having from 5 to about 10 carbon atoms.

10. A process according to claim 2 wherein said oleum comprises a mixture of sulfuric acid and sulfur trioxide wherein the weight percent sulfur trioxide therein is in the range of about 5 to 65 percent.

11. A process for preparing m,m'-dinitrobenzophenone which comprises reacting benzophenone with nitric acid and oleum to form a first reaction product;

adding a sufficient amount of water to said first reaction product to form a second reaction product so that the total amount of free water in the second reaction product is from about 12 to about 30 weight percent of such second reaction product;

contacting said second reaction product with a solvent extracting amount of a chlorinated hydrocarbon having from one to six carbon atoms under solvent extraction conditions;

separating said chlorinated hydrocarbon containing m,m'-dinitrobenzophenone; and recovering m,m'-dinitrobenzophenone.

12. A process for preparing m,m'-dinitrobenzophenone which comprises:

reacting benzophenone with nitric acid and oleum to form a first reaction product;

passing said first reaction product to a solvent extraction zone;

adding to said first reaction product a solvent extracting amount of a chlorinated hydrocarbon having from one to six carbon atoms in said solvent extraction zone;

adding a sufficient amount of water to said solvent extraction zone so that the total amount of free water in said solvent extraction zone is from about 12 to about 30 weight percent of the solvent-free material in said solvent extraction zone product and thereafter contacting said first reaction product with said chlorinated hydrocarbon under solvent extraction conditions;

separating said chlorinated hydrocarbon from said first reaction product; and recovering m,m'-dinitrobenzophenone from said separated chlorinated hydrocarbon.

13. A process according to claim 12 wherein the weight ratios of benzophenone, sulfuric acid and sulfur trioxide in said oleum are in the range of about 1:2:2 to about 1:15:4.

14. A process in accordance with claim 12 wherein said chlorinated hydrocarbon has from two to four chlorine atoms.

15. A process in accordance with claim 12 wherein said chlorinated hydrocarbon is 1,2-dichloroethane.

16. A process in accordance with claim 12 wherein the volume ratio of said chlorinated hydrocarbon to said first reaction product is from 0.5:1 to 10:1.

17. A process in accordance with claim 12 wherein said m,m'-dinitrobenzophenone is recovered by precipitating the dinitrobenzophenone is a hydrocarbon non-solvent.

18. A process in accordance with claim 12 wherein at least a portion of said chlorinated hydrocarbon is removed prior to contact with said non-solvent.

19. A process in accordance with claim 12 wherein from about 40 to about 70 volume percent of the chlorinated hydrocarbon is removed prior to contact with said non-solvent.

20. A process in accordance with claim 12 wherein the non-solvent is a hydrocarbon having from 5 to about 10 carbon atoms.

21. A process according to claim 12 wherein said oleum comprises a mixture of sulfuric acid and sulfur trioxide wherein the weight percent sulfur trioxide therein is in the range of about 5 to 65 percent.

* * * * *